| United States Patent [19] | [11] | Patent Number: | 4,837,189 |
|---|---|---|---|
| Simon et al. | [45] | Date of Patent: | Jun. 6, 1989 |

[54] SURFACTANT MODIFIED METAL CATALYSTS

[75] Inventors: Helmut Simon, Freising; Jordanes Thanos, Munich, both of Fed. Rep. of Germany

[73] Assignee: BASF Aktiengesellschaft, Rheinland-Pfalz, Fed. Rep. of Germany

[21] Appl. No.: 163,538

[22] Filed: Mar. 3, 1988

Related U.S. Application Data

[62] Division of Ser. No. 939,118, Dec. 8, 1986, Pat. No. 4,749,670.

[30] Foreign Application Priority Data

Jan. 8, 1986 [DE] Fed. Rep. of Germany ....... 3600274

[51] Int. Cl.$^4$ .................... B01J 31/02; B01J 31/28; C12P 7/52
[52] U.S. Cl. .................................. 502/150; 435/141; 435/146; 435/158; 502/173; 502/185
[58] Field of Search ................ 502/150, 159, 173, 339

[56] References Cited

U.S. PATENT DOCUMENTS

| 4,176,026 | 4/1979 | Harriman et al. | 204/157.52 |
| 4,211,621 | 7/1980 | Porter | 204/157.52 |
| 4,367,131 | 1/1983 | Gratzel et al. | 502/173 |
| 4,394,293 | 7/1983 | Gratzel et al. | 502/159 |
| 4,425,261 | 1/1984 | Stenius et al. | 502/339 |
| 4,464,235 | 8/1984 | Simon et al. | 204/73 R |
| 4,526,661 | 7/1985 | Steckhan et al. | 204/73 R |

OTHER PUBLICATIONS

J. Electroanal. Chem. 235 (1987), pp. 131–152, "Mechanical Aspects of Reaction Selectivities on Surfactant-Modified PD and PT Electrodes and Catalysts", I. Thanos.

Angewandte Chemie, vol. 25, No. 5, May 1986, pp. 462–463, "Stereospecific Reductions with Hydrogen Gas Modified Metal Catalyst, Methyl Viologen and Enzymes or Microorganisms", by I. Thanos and H. Simon.

J. Chem. Soc.-Faraday Trans. II—Nov. 1982, pp. 1955–1970–"Colloidal Platinum Catalysts for Photoredox Processes", Harriman et al.

*Primary Examiner*—Paul E. Konopka
*Attorney, Agent, or Firm*—Oblon, Fisher, Spivak, McClelland & Maier

[57] ABSTRACT

Surfactant-modified metal catalysts which can be used in a process for hydrogenating mediators.

7 Claims, No Drawings

SURFACTANT MODIFIED METAL CATALYSTS

This is a division of application Ser. No. 06/939,118, filed Dec. 8, 1986, now U.S. Pat. No. 4,749,670.

The present invention relates to a process for the catalytic hydrogenation of mediators (electron carriers) with the aid of special catalysts, and to these catalysts.

It is known that electrons can be transferred to biochemical redox enzymes with the aid of mediators, which are also referred to as electron carriers. For this purpose, the mediators have to be reduced continuously. This has been effected to date with hydrogen in the presence of a hydrogenase, formate in the presence of a vilogen-dependent formate dehydrogenase (Angew. Chem. 97 (1985), 541 and 617, and Angew. Chem. Int. Ed. Engl. 24 (1985), 539 and 617 or electrochemically (European Laid-Open Application 99,517). The first two processes have the disadvantage that it is necessary to use a second enzyme, which as a rule is sensitive. The electrochemical reduction requires very expensive apparatus.

Viologens can also be reduced with zinc or dithionite (J. Amer. Chem. Soc. 107 (1985), 2632) or with hydrogen and platinum on asbestos (J. Biol. Chem. 249 (1974), 1572). However, these processes cannot be carried out continuously since the zinc or dithionite is consumed, and the methyl viologen cannot be regenerated as often as desired with platinum, because the methyl viologen is relatively rapidly destroyed. Furthermore, metal cations and sulfite anions which accumulate during the reaction interfere with the enzyme reactions. We have found that mediators, such as methyl viologen, can be very readily hydrogenated using certain catalysts.

The present invention relates to a process for the selective regeneration of mediators by catalytic hydrogenation, wherein the catalyst used is a metal catalyst modified with the aid of surfactants, and to these modified catalysts.

The hydrogenation is carried out under a hydrogen atmosphere under atmospheric or slightly above atomspheric pressure in the absence of oxygen. The temperature and the pH during the reaction depend on the enzyme used. As a rule, the reaction is carried out at from 10° to 90° C., preferably from 25°–40° C., and at a pH of from 3 to 10, preferably from 5 to 8.

The following substances are suitable mediators:
1. Viologen dyes, e.g. methyl viologen, benzyl viologen, carboxamidomethyl viologen and diquat,
2. Anthraquinone and other quinone dyes, eg. phenosafranin, methylene blue and anthraquinonesulfonic acids,
3. Triphenylmethane dyes, eg. methyl violet and crystal violet,
4. Phthalocyanines, eg. Fe, Cu and Co phthalocyanine,
5. Methine dyes, eg. astraphloxin,
6. Pyrrole dyes and porphyrin derivatives, eg. metal chelate complexes of these compounds,
7. Pteridines and pteridones,
8. Flavines, eg. acriflavine and lumiflavine, and
9. Complexes of metals of subgroups 6, 7 and 8, eg. $Ru(L_2L'_2)^{++}$ [L=1,10-phenanthroline, 2,2-bipyridyl or 5-nitro-1,10-phenanthroline and L' =pyridine or 4-methylpyridine], 1,1'-bis(hydroxymethyl)-ferrocene and ferrocenemonocarboxylic acids.

Among these, the first group is preferred, in particular methyl viologen and benzyl viologen.

Suitable surfactants are those which have good wetting properties on metal surfaces, in particular those whose hydrocarbon radicals are highly fluorinated. Fluorine-containing cationic surfactants, as obtainable under the name $^{(R)}$Zonyl, are particularly suitable. The best effect was obtained with the surfactant $^{(R)}$Zonyl FSC, which is said to have the structure $[F(CF_2-CF_2)_{3-8}-CH_2-CH_2-S-CH_2-CH_2-N(CH_3)_3]^+CH_3SO_4^-$. A neutral surfactant having the name $^{(R)}$Zonyl FSB and a basic surfactant ($^{(R)}$Zonyl FSA) are also very useful.

Particularly suitable modifiable metal catalysts are nickel and noble metals, such as palladium and platinum.

To prepare the modified catalyst, the stated metal, preferably in the hydrogenated form, is suspended in water or a buffer (0.2–1.0 ml per mg of metal) under a hydrogen atmosphere, 2–5 times the weight (based on the metal) of surfactant are added and the mixture is shaken or stirred for about 10–30 hours at about 20°–40° C. Thereafter, the modified catalyst is separated off, for example by centrifuging or decanting, and is stored in the absence of oxygen. It neet not be dried. In the presence of oxygen, it slowly becomes deactivated.

In the presence of the surfactants, the metal catalysts are altered so that they reduce only the mediators but not unsaturated compounds and cosubstrates, such as NAD (P), etc. The mediators are not overreduced and therefore remain stable. Furthermore, in contrast to unmodified metal catalysts, surfactant/metal catalysts do not attack pyridine nucleotides which may be present in redox systems.

The novel catalyst makes it possible to carry out a large number of biochemical reductions with hydrogen. The electrons of the hydrogen are first transferred to the mediator, which then passes these electrons on to hydrogen-transferring enzymes which reduce a substrate. The novel catalyst is not capable of transferring the hydrogen directly to the substrate. Hence, if compounds possessing centers of asymmetry are formed during the reduction, the selectively of the reaction is determined exclusively by the enzyme specificity.

Compared with the previous processes, the novel process also has the advantage that neither an enzyme nor an electrochemical cell is required for the formation of reduced mediator.

Finally, it should also be stated that the novel system is useful for regenerating not only isolated enzymes but also non-isolated enzymes in entire microorganisms. (A) Preparation of modified catalysts

EXAMPLE 1

(a) Modified palladium 30 mg of 10% palladium on carbon (Merck) in 20 ml of 0.1 M phosphate buffer at pH 7.5 were gassed with nitrogen and saturated under hydrogen. After the addition of 120 μl of $^{(R)}$Zonyl FSC or FSB, the mixture was shaken at 35° C. for 10 hours at about 120 oscillations per minute, under an $H_2$ asmosphere. The catalyst can be substantially freed from the detergent by removing it by centrifuging and suspending it again in the desired buffer or volume. On the basis of experience to date, however, the surfactant content does not have an adverse effect during the further reactions. For long-term storage of the modified catalyst (more than 6 months), tris. HCL buffer is better than potassium phosphate.

(b) Modified platinum or nickel 35 mg of finely divided platinum obtained by hydrogenating platinum dioxide were shaken, in 8 ml of 0.1 M potassium phosphate buffer at pH 7.5, with 150 μl of (R)Zonyl FSC at 35°C. for 15 hours under hydrogen gas. Like the platinum, nickel obtained by dissolving a nickel-aluminum alloy with sodium hydroxide solution and washing neutral was treated with hydrogen gas. (B) Comparative experiments

EXAMPLE 2

The experiments below demonstrate the changed behavior of modified palladium and platinum toward methyl viologen in comparison with unmodified catalysts.

3.5 mg of palladium modified according to Example 1 and unmodified palladium, in separate batches, were shaken in 3.1 ml of 0.1 M tris. HCL buffer at pH 7.2 in the presence of 30 mmol of methyl viologen under hydrogen at 35° C. In the batch containing modified palladium, more than 98% of the methyl viologen was still present after 4 days, whereas the batch containing the unmodified palladium contained less than 1.5% of methyl viologen after 2 days. 1,1'-carboxamidomethyl viologen showed the same stability.

(C) Use of the catalyst

EXAMPLE 3

(a) Preparation of (2R)-methylbutyric acid using enoate reductase, hydrogen gas and modified palladium 12 mg of palladium modified according to Example 1 were stirred in 10 ml of potassium phosphate buffer at pH 7.0 together with 0.04 mmol of methyl viologen hydrochloride, 0.8 mmol of the sodium salt of (E)-2methylbutenoate and 2 units of enoate reductase under an $H_2$ atmosphere at 27° C. and under atmospheric pressure. After about 15 hours, the conversion was more than 98%. After extraction with diethyl ether, some of the product was reacted with (R)-phenylglycinol to give the corresponding amide. According to HPLC analysis, the enantiomeric purity of the amide (enantiomeric excess) was more than 97%.

If the enoate reductase is omitted, the reaction does not take place.

If the reaction is carried out without enoate reductase but in the presence of unmodified palladium, racemic methylbutyric acid is obtained.

(b) By means of a similar procedure, (2R)-2-methyl-3-phenylpropionic acid was obtained from (E)-2-methylcinnamate in the same yield and enantiomeric purity.

EXAMPLE 4

Reduction of cinnamate to 3-phenylpropionate using modified platinum, hydrogen gas and enoate reductase.

7.5 mg of modified platinum, 3.3 mmol of methyl viologen and 70 mmol of cinnamate were added to 3.0 ml of 0.12 M tris. HCL buffer at pH 7.0. The system was shaken at 35° C. under an $H_2$ atmosphere, the solution rapdily becoming blue. The amount of hydrogen consumed was equal to that required for the reduction of the methyl viologen, ie. about 5 μmol. Thereafter, no further consumption of hydrogen was observed for 4 hours. 1.3 units of enoate reductase were then added and hydrogen was passed in again, leading to quantitative reduction of the cinnamate in 5 hours. The solution was shaken for a further 10 days, the methyl viologen remaining unchanged.

EXAMPLE 5

Reduction of (2R)-2-hydroxy-4-methylpentanoate using partially purified 2-oxo acid reductase, hydrogen gas and modified palladium 30 mg of modified palladium were shaken in 50 ml of 0.1 M phosphate buffer at pH 7.0 together with 0.2 mmol of methyl viologen, 5 mmol of 2-oxo-4-methylpentanoate and 8 units of partially purified 2-oxo acid reductase under an $H_2$ atmosphere at 25° C. The conversion was higher than 985 after 40 hours, after which the (2R)-2-hydroxy-4-methylpentanoate was isolated and the optical rotation $[\alpha]589/$ RT was determined as $+10.9°$ (c=22 mg/ml). This corresponds to an enantiomeric excess of more than 95%.

EXAMPLE 6

Preparation of (2R)-propanediol using yeast, hydrogen gas and modified palladium 7 mg of palladium modified according to Example 1 were stirred in 10 ml of 0.1 M phosphate buffer at pH 7.3 with 0.03 mmol of methyl viologen, 0.01 mmol of NAD, 140 mg of Cadida utilis (DSM 70 167) and 1 mmol of hydroxyacetone under an $H_2$ atmosphere at 25° C. After 9 hours, and after the consumption of an appropriate amount of hydrogen, the yield of propanediol was 90%.

A corresponding experiment without the addition of NAD took 13 hours but gave the same yield.

We claim:

1. A modified metal catalyst, for use in hydrogenation reactions, wherein said modified metal catalyst is prepared by a process comprising the steps of:
    (i) suspending a modifiable metal catalyst selected from the group consisting of nickel and noble metals in water or in a buffer solution under a hydrogen atmosphere;
    (ii) adding to said suspension 2–5 times the weight, based on said metal catalyst, of a fluorine-containing surfactant, wherein said surfactant has good wetting properties on metal surfaces, to prepare a metal catalyst/surfactant mixture;
    (iii) shaking or stirring said mixture to prepare said modified catalyst; and
    (iv) separating out said modified catalyst.

2. The modified catalyst of claim 1, wherein said modified catalyst is not capable of transferring hydrogen directly to a hydrogenation substrate.

3. The catalyst of claim 1, wherein said metal catalyst is palladium or platinum.

4. The catalyst of claim 1, wherein said surfactant is selected from the group consisting of $R_fCH_2CH_2SCH_2CH_2CO_2Li$, $(R_fCH_2CH_2O)_{1,2}P(O)(ONH_4)_{2,1'}$ $(R_fCH_2CH_2O)_{1,2}P(O)(OH)_{2,1'}$ $R_fCH_2CH_2SCH_2CH_2N^+(CH_3)_3CH_3SO_3^-$, $R_fCH_2CH_2O(CH_2CH_2O(CH_2CH_2O)_xH$, $R_fCH_2CH(OCOCH_3)CH_2N^+(CH_3)_2CH_2CO_2^-$, flouroalkyl poly(ethylenoxide)ethanol, and mixtures thereof with non-fluorinated surfactants, wherein $R_f$ is $F(CF_2CF_2)_{3-8}$.

5. The catalyst of claim 1 wherein said suspending step comprises adding 0.2–1.0 ml of water or buffer per mg of metal catalyst.

6. The catalyst of claim 1, wherein sais mixture is shaken or stirred for about 10–30 hours at about 20°–40° C.

7. The catalyst of claim 1, wherein said separating step comprises centrifuging or decanting.

* * * * *